United States Patent [19]

Hall

[11] Patent Number: 4,695,417
[45] Date of Patent: Sep. 22, 1987

[54] METHOD OF MAKING AN OPTICALLY CLEAR TOOTH POSITIONING AND RETAINING APPLIANCE

[75] Inventor: Arthur B. Hall, LaPorte, Ind.

[73] Assignee: TP Orthodontics, Inc., Westville, Ill.

[21] Appl. No.: 443,472

[22] Filed: Nov. 22, 1982

[51] Int. Cl.[4] ...................... B29C 39/00; B29C 59/08
[52] U.S. Cl. ........................................ 264/80; 264/16; 264/162
[58] Field of Search ............................ 264/16, 80, 162

[56] References Cited

U.S. PATENT DOCUMENTS

| 1,667,146 | 4/1928 | Drake | 65/120 |
|---|---|---|---|
| 2,665,568 | 1/1954 | Meyer et al. | 264/348 |
| 2,746,084 | 5/1956 | Kreidl | 264/80 |
| 2,775,036 | 12/1956 | Kesling | 433/6 |
| 2,795,820 | 6/1957 | Grow et al. | 264/80 |
| 3,224,441 | 12/1965 | Monaghan | 128/136 |
| 3,361,607 | 1/1968 | Bruno | 264/80 |
| 3,379,193 | 4/1968 | Monaghan | 128/136 |
| 3,702,789 | 11/1972 | Dungan | 264/80 |
| 3,724,075 | 9/1973 | Kesling | 433/11 |
| 3,808,301 | 4/1974 | Pruden | 264/80 |
| 3,837,081 | 11/1974 | Kesling | 433/6 |
| 4,044,762 | 8/1977 | Jacobs | 264/16 |
| 4,067,942 | 1/1978 | Wilson | 264/80 |
| 4,195,046 | 4/1980 | Kesling | 264/16 |

FOREIGN PATENT DOCUMENTS

| 2504447 | 10/1982 | France | 264/80 |
|---|---|---|---|
| 46-19190 | 4/1971 | Japan | 264/80 |

OTHER PUBLICATIONS

"Simplified Positioner Construction", by Drs. Rakosi, Jonas and Burgert, Journal of Clinical Orthodontics, vol. 15, No. 3, Mar. 1981, pp. 206–208.

Randolph et al., Plastics Engineering Handbook, Reinhold, N.Y. (1960), p. 44.

*Primary Examiner*—Willard E. Hoag
*Attorney, Agent, or Firm*—Lloyd L. Zickert

[57] ABSTRACT

A method of making an optically clear custom tooth positioning and retaining appliance in a flask or mold device having mold members from an elastomeric or resilient thermoplastic material with the capability of having optically clear transparentness, after the appliance has been trimmed and/or buff polished subsequent to molding thereof which causes the appliance to have a frosty or translucent appearance, which method includes subjecting the exterior surfaces of the appliance to a source of concentrated heat to cause surface melting which produces transparentness, cooling the appliance before, during and after heating as needed to preserve its integrity, and optionally utilizing the mold members from the flask or reproductions thereof in the archways of the appliance during heating thereof.

13 Claims, 10 Drawing Figures

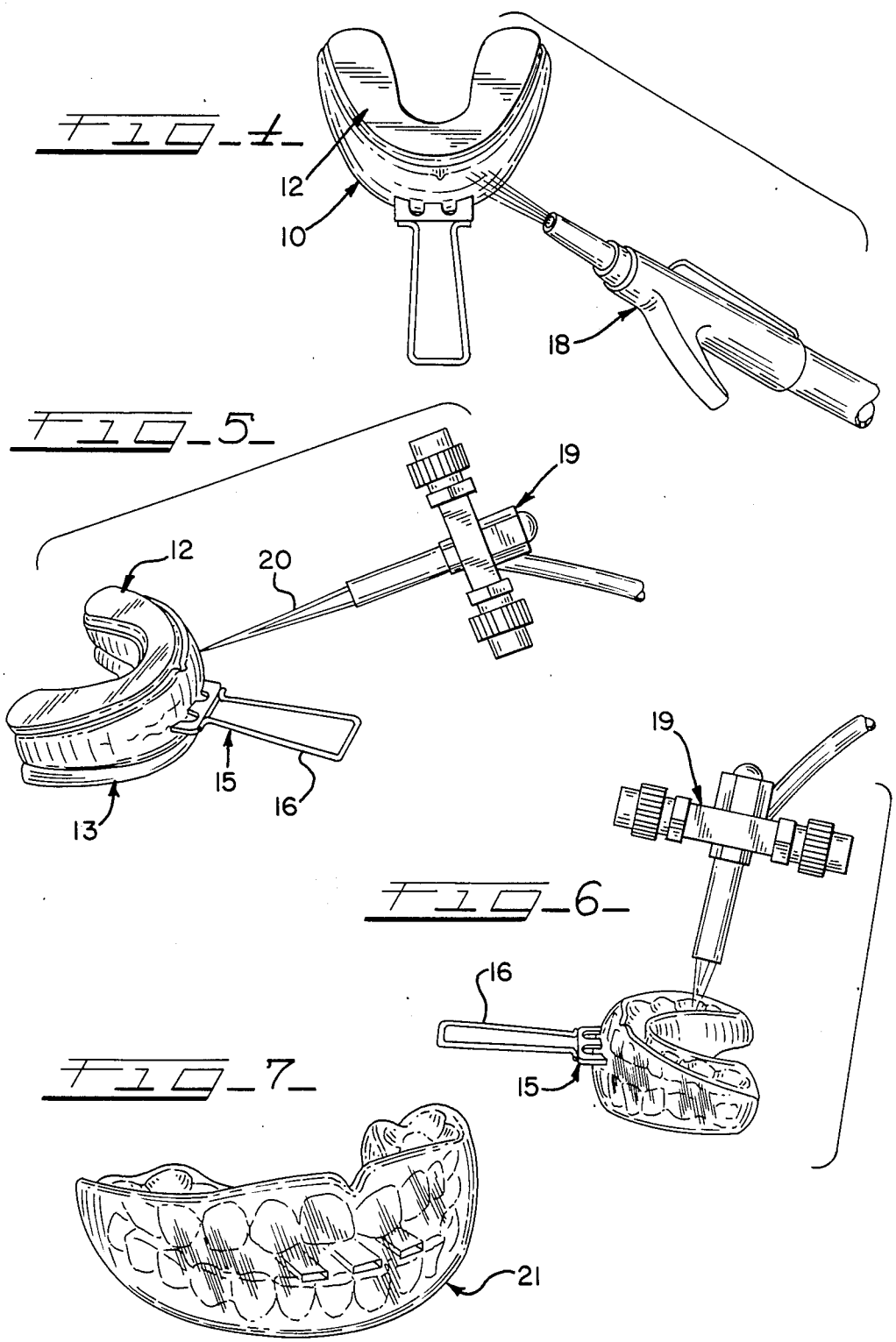

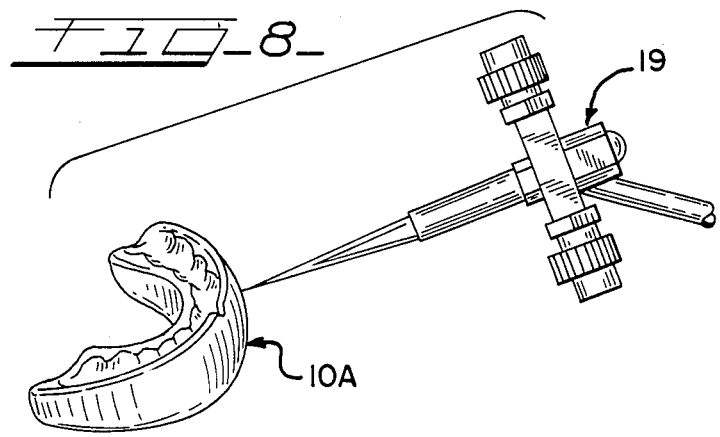
FIG_8_
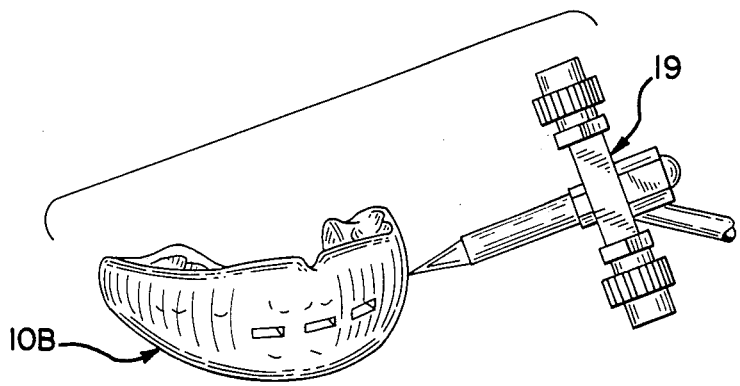
FIG_9_
FIG_10_
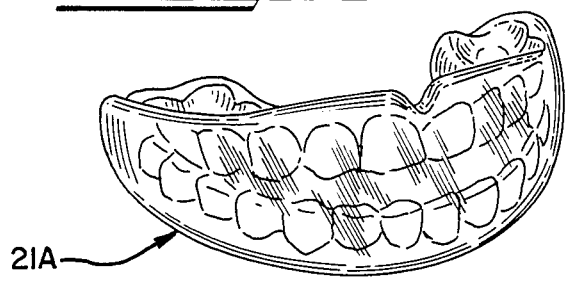

METHOD OF MAKING AN OPTICALLY CLEAR TOOTH POSITIONING AND RETAINING APPLIANCE

This invention relates in general to a method for treating a trimmed and/or buff polished custom tooth positioning and retaining appliance molded from a resilient thermoplastic material with the capability of having substantially optically clear transparentness which has a frosty appearance or translucent surface so that it thereafter becomes transparent.

BACKGROUND OF THE INVENTION

The use of tooth positioning and retaining appliances in the orthodontic treatment of patients is well known. Such appliances are both custom made and preformed. An apparatus and method for making custom appliances is disclosed in U.S. Pat. No. 2,775,036. Preformed appliances are disclosed in U.S. Pat. Nos. 3,724,075 and 3,837,081. The latter two patents also make it well known to use a resilient thermoplastic material for making such appliances. Such material having the capability of being optically clear has also been known. It is also well known to mold air holes or airways in such appliances, as disclosed in U.S. Pat. No. 4,195,046.

Both U.S. Pat. Nos. 2,775,036 and 4,195,046 teach the method and apparatus for making custom tooth positioning and retaining appliances where a three-part dental flask is employed, the central part of which co-acts with upper and lower parts. The central part receives a blank of moldable material which upon being heated and being subjected to mold members mounted in the upper and lower parts becomes a custom-molded appliance. Following the removal of the molded appliance from the flask, it must be trimmed and/or buff polished before it is ready to be used by a patient.

Custom-made resilient plastic appliances have been available with shiny surfaces, but such appliances are not optically clear. It has also been known to provide preformed appliances molded of resilient thermoplastic material that are substantially optically clear, but those appliances are never subjected to trimming and/or buff polishing.

Heretofore, it has also been known to make custom appliances from a thermosetting resilient material such as rubber and other thermosetting plastics, however, none of which are optically clear after being trimmed and/or buffed. Mainly for aesthetic reasons, certain orthodontists prefer to use for their patients what has been heretofore defined as a transparent appliance made generally by a thermoplastic material, but which is semi-opaque or frosty in appearance and actually translucent. Accordingly, it has not been possible to heretofore provide the custom-made appliance that has been subjected to trimming and/or buff polishing to be truly transparent or optically clear. Thus, such a preferred appliance, long desired by orthodontists has not been available.

SUMMARY OF THE INVENTION

The present invention overcomes the difficulties heretofore encountered in the attempts to provide an optically clear and transparent custom-made tooth positioning and retaining appliance. The present invention makes an appliance having a semi-opaque or frosty appearance substantially optically clear and transparent where the appliance is molded from a resilient or elastomeric thermoplastic material having the capabilities of becoming optically clear. The frosty appearance is caused by the need to trim by abrasive grinding and/or buff polish the appliance subsequent to molding. The method of the invention includes the steps of cooling the appliance thoroughly and subjecting the exterior surfaces to a concentrated source of heat such that surface melting is effected to produce a shiny appearance. Heating may be intermittently applied between cooling cycles. The shiny appearance indicates the appliance to be optically clear. Optionally, the mold members from the flask used to make the custom appliance or reproductions of those mold members may be positioned in the archways of the appliance prior to the cooling and heating steps.

Subjecting the appliance to a concentrated heat source may be accomplished by using a concentrated blue flame generated from gas or a mixture of gas and air. Such treatment will be sometimes referred to as flame polishing. Suitable means may be employed to support the appliance with the mold members during the flame polishing, although it is possible to manually hold the appliance. For example, where the appliance has molded airways or air holes, an air hole insert with a handle may be associated with the air holes to support the appliance and/or mold members such that the handle may be grasped by the technician who flame polishes or otherwise applies a concentrated heat source to the appliance and cools the appliance. If no air holes are provided, handle means may be attached to one or both mold members for supporting the appliance during the heat treating step or the asembly may be manually gripped by the molding members. Optionally, the archways of the appliance may be also be heat treated such as by flame polishing upon removal of the mold members if they are used to further enhance optical clarity.

It is therefore an object of the present invention to provide a new and improved method for making a custom tooth positioning and retaining appliance molded from a resilient thermoplastic material so that it is transparent and essentially optically clear, thereby making the appliance more aesthetically acceptable to a patient to enhance patient cooperation and to also more readily permit visual examination of positioner placement on the teeth of a patient.

A further object of the invention is to provide a method of treating a trimmed and/or buff polished custom tooth positioning appliance molded of an elastomeric thermoplastic material having a translucent appearance but being capable of being transparent which includes subjecting the exterior surfaces of the appliance to a concentrated source of heat that causes surface melting and produces transparentness in the appliance, while maintaining the bulk of the appliance at a temperature below the softening temperature.

A still further object of the present invention is to make a substantially transparent custom tooth positioning appliance that improves patient cooperation and permits the orthodontist to visually examine the appliance in place to better determine its fit.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 4 is a perspective view illustrating the step of blow drying the appliance and molding parts subsequent to removing them from the cooling medium;

FIG. 5 is a perspective view illustrating the step of applying a concentrated heat source by flame polishing the labial side of the appliance with an air-gas blow pipe;

FIG. 6 illustrates the step of flame polishing the archways of the appliance;

FIG. 7 is a perspective view of the appliance after it has been fully treated and illustrating it to be optically clear;

FIG. 8 is a perspective view illustrating the step of applying a concentrated heat source to the labial side of an appliance with an air-gas blow pipe which does not include air holes and where the use of molding members has been omitted;

FIG. 9 is a perspective view similar to FIG. 8 but illustrating the appliance with air holes and with the heat source applied to another part of the appliance; and FIG. 10 is a perspective view of the appliance after it has been treated by the method of the invention and illustrating it to be optically clear and transparent.

DESCRIPTION OF THE PREFERRED EMBODIMENTS

The method of the present invention concerns the treatment of a custom-made tooth positioning and retaining appliance which is constructed of a resilient thermoplastic material with the capability of having substantially optically clear transparentness. Such an appliance has been heretofore made and sold and represented to be clear when in fact it has a semi-opaque or frosty appearance. Treatment of that appliance by the method of the present invention results in the production of an appliance which is substantially optically clear and therefore transparent. The use of such an appliance treated according to the invention, because it has greater aesthetic appeal, is expected to have a major impact on improving patient cooperation. Moreover, the transparency of such an appliance readily permits the orthodontist to visually examine the appliance in place in a patient's mouth to determine proper positioner placement. This thereby facilitates the effectiveness of orthodontic treatment.

Figure 1:
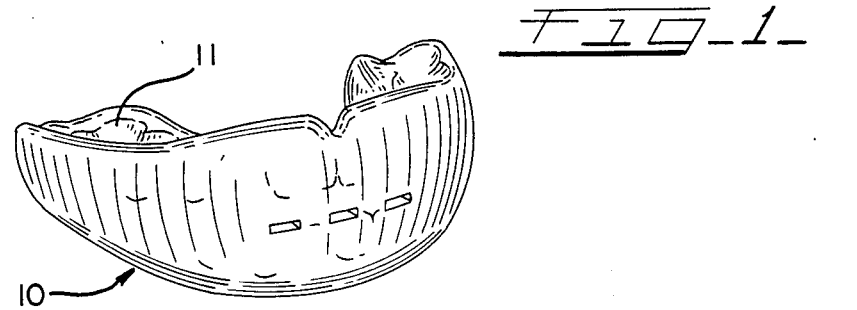
FIG. 1 is a perspective view of a tooth positioning and retaining appliance subsequent to being trimmed and buff polished where it has a semi-opaque or frosty appearance.

The apparatus and method of making a custom-made tooth positioning and retaining appliance of the type illustrated in FIG. 1 is fully disclosed in U.S. Pat. Nos. 2,775,036 and 4,195,046. For purposes of better understanding the present invention, reference will be made to these patents and particularly to the latter patent.

The material employed for making such an appliance is either an elastomeric thermosetting or thermoplastic material. The material is generally formed or premolded into a blank in the form of a bar or in the form of a horseshoe so that it can be readily used in the apparatus and method for making a custom appliance. As disclosed in U.S. Pat. No. 4,195,046, such a blank is inserted into the central section of a mold or flask which coacts with upper and lower sections, each of which has mounted therein mold members in the form of a patient's upper and lower arches which previously have been made from a setup that arranges the teeth in an ideal arch relationship. It may be appreciated that prior to treating a patient with such an appliance, the patient has already been treated for a time with fixed appliances and that the tooth positioning and retaining appliance is used in the final treatment stage of a patient to bring the teeth into the ideal arch relationship.

The mold members in the mold or flask which are representative of the teeth in the ideal relationship are made of a suitable plaster or stone so that they can withstand the heat and pressure needed when the mold members are brought together with the blank of molding material. Subsequent to the molding operation, after the archways are properly formed in the blank of material to form the appliance in its initial phase, the appliance is then removed from the flask and trimmed and optionally buff polished in the usual manner to provide the appliance, as shown in FIG. 1. Trimming is accomplished by subjecting the appliance to either or both coarse and fine grinding wheels. Thereafter, the appliance may be cooled and removed from the mold set for trimming and buffing.

The present invention requires choosing an elastomeric or resilient thermoplastic material that is or can be optically clear or transparent. One example of such a material is a family of commercially available resins which are a copolymer of ethylene and vinyl acetate.

Figure 2:
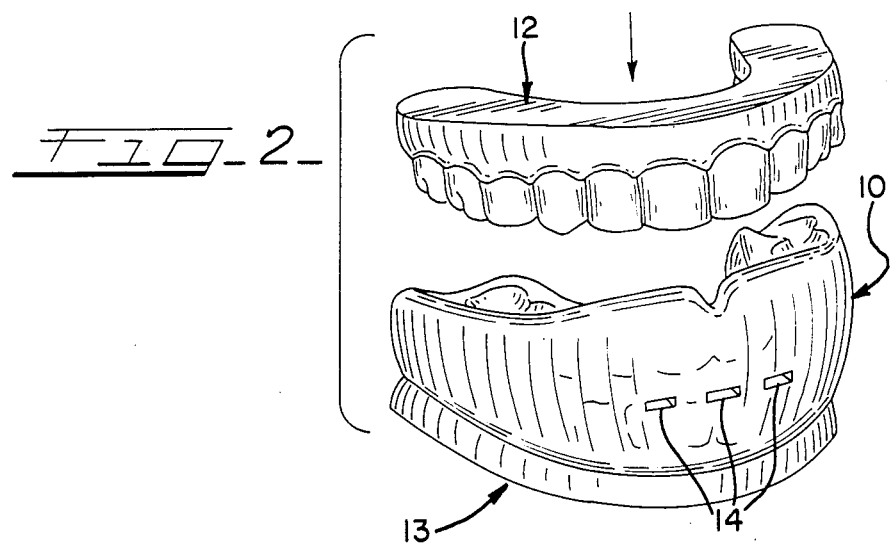
FIG. 2 is a perspective view of the appliance of FIG. 1 illustrating the optional application of the molding members to the appliance as a step in the method of making it substantially optically clear according to the invention.

One method of making the appliance optically clear according to the present invention includes the step of salvaging the plaster or stone arches or models used in the flask as mold members to mold the archways into the appliance. As seen particularly in FIG. 1, the appliance with a semi-opaque appearance is designated by the numeral 10 and a part of the upper archway 11 is seen, but it will be understood that it will likewise have a lower archway representative of the lower arch of the patient for which the appliance is being made. The plaster or stone arches or models used to mold the appliance in the flask are illustrated in FIG. 2, the upper being designated by the numeral 12 and the lower by the numeral 13. In the event that it is not possible to salvage these models from the flask, new models or reproductions of the arches may be made from the setup by any suitable method or the setup may be used in the method of making the appliance optically clear. In the event the appliance is made with seating springs of the type illustrated in the preformed appliance of U.S. Pat. No. 3,837,081, it may be necessary to redrill seating spring holes in the upper and/or lower stone models 12 and 13 prior to positioning the models relative to the appliance in order to provide accurate seating of the models on the appliance. Use of the models with the appliance during the further treatment of the appliance enhances the stability of the appliance when it is being subjected to heat to prevent distortion, and also assists in dissipating heat generated during the heating step.

If molded airways or air holes are provided in the appliance 10 as illustrated at 14, an air hole insert support 15 may be used to facilitate the flame polishing step. The manner in which air holes may be molded into the appliance is fully disclosed in U.S. Pat. No. 4,195,046. These air holes are disposed in the appliance between the upper and lower archways and extend between the labial and lingual sides of the appliance.

Figure 3:
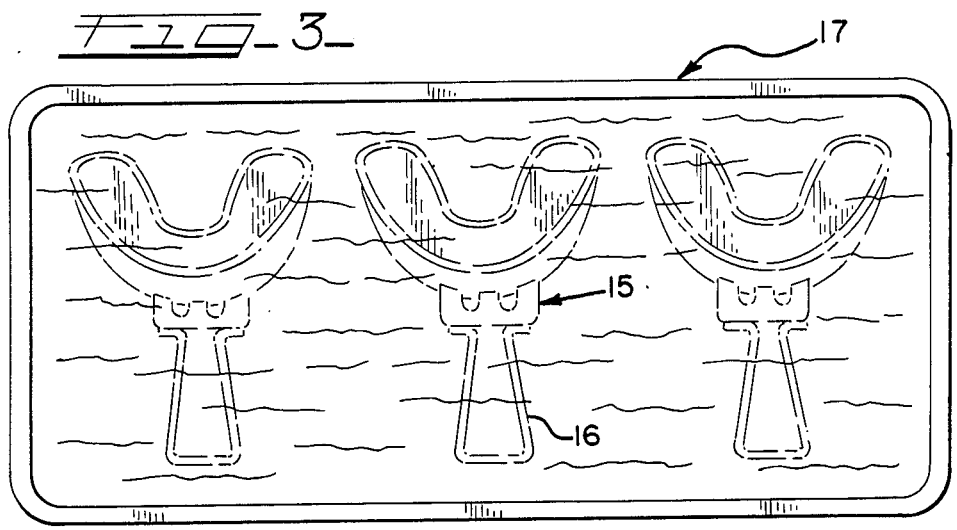
FIG. 3 illustrates the step of cooling the appliance and the molding members where they are immersed in a cooling medium such as water and also illustrating the air hole inserts in place which facilitates the handling of the assembly of the appliance and molding parts during treatment by flame polishing.

While the illustrations herein show the use of an air hole insert support because air holes have been provided, if such air holes are not molded into the appliance, the appliance with the models may be handled by manually grasping the outer portions of the models or by mounting a handle on one or more of the models for facilitating the supporting of the appliance during the heating step. So, where air holes are provided following the step of mounting the models onto the appliance, the air hole insert support 15 which includes a handle 16 is mounted on the appliance by inserting the fingers of the support into the air holes as illustrated. Thereafter, the assembly of the appliance, models and air holes insert support is cooled such as by placing this assembly into a container 17 of cool or cold water to room temperature or below, as illustrated in FIG. 3. This step not only wets the models but also cools them so that they can thereafter better dissipate heat during the heating step. However, it may be appreciated the assembly may be cooled by other methods if desired.

Following the cooling of the assembly, it is necessary to next remove the water and therefore the assembly is blow dried, as illustrated in FIG. 4, by use of a suitable air nozzle 18 connected to a source of compressed air. The overall assembly is now prepared for the step of heating which may also be deemed heat polishing.

The step of heat polishing is preferably accomplished by the use of a gas-air blow pipe 19 that is suitably connected to a source of flammable gas and air which coacts to produce a concentrated pencil-thin blue flame 20 which is quite hot. The heat polishing for making the appliance transparent may be here defined as flame polishing. When properly adjusted, the pipe will produce a flame having a temperature of about 5700 degrees F. The blow pipe is adjusted to generate a flame having a height of one to one-and-one-half inches. At its base the flame will be about one-quarter inch in diameter and will taper to a pinpoint. While it is preferable to use a gas-air blow pipe, it may be appreciated that any device which will produce a concentrated blue flame will be acceptable to carry out the step of flame polishing.

The step of flame polishing involves the application of the apex or pinpoint of the flame to the outer or labial surface of the appliance, as generally illustrated in FIG. 5, and preferably moving the flame from the distal toward the mesial until the material of the appliance begins to shine and transparency through the appliance may be observed. The temperature of the appliance material at the surface must be raised to cause momentary melting to smooth the surface so that it is transparent. It is important, where an air hole insert is used, to minimize the heat from the flame such that it does not go directly onto the insert. In addition to the insert serving to assist in supporting the entire assembly, the insert will provide stability for the air holes so that they do not close. The flame may be applied above the insert in the first instance, and in order to avoid overheating, the entire assembly can be immersed in water or other suitable cooling medium and then blow dried. Then, the flame can be applied beneath the insert to the other part of the labial surface, and once again the assembly can be immersed in cool water to cool it. Thereafter, it must again be blow dried before further flame polishing. Similarly, the lingual surface of the appliance will be flame polished by application of the apex of the flame to the lingual surface of the appliance and moving it therealong until the material begins to shine and become transparent. It is then again cooled to stabilize the material.

In order to obtain maximum transparency, the archways, which include the tooth sockets and gum areas, may also be flame polished. The size of the flame is readjusted such that it is about two-thirds the original height, although a well defined primary blue flame must still be present. The models 12 and 13 are removed following the cooling of the appliance in water and blow drying. The flame should be held above the center of the tooth sockets and quickly moved around the arch from one end to the other end. Thereafter, the positioner may be immediately dropped in water for cooling purposes. After blow drying the appliance, the opposite archway may then be flame polished in the same manner.

Following the optional flame polishing of the archways, the appliance then attains its maximum optical clarity and transparentness, as illustrated by the appliance designated as 21 in FIG. 7. Upon removal of the air hole insert support, the appliance may then be checked by placing it on the setup. It can then be sent to the orthodontist for placement with a patient.

The method of treating a trimmed and/or buff polished appliance to obtain optical clarity may be achieved without the use of the mold members in the archways of the appliance during the flame polishing step or steps. This method is illustrated particularly in FIGS. 8 to 10 wherein a trimmed and/or buffed appliance 10A is shown in FIG. 8 with the pinpoint flame of a gas-air blow pipe 19 being applied to its labial surface. The appliance 10A also differs from the appliance illustrated in FIG. 1 in that it does not include air holes. An appliance with air holes and being flame polished without use of the mold members is illustrated in FIG. 9 and designated 10B. Moreover, it should be appreciated that during the flame polishing steps, the appliance may be supported by manually grasping it at one end during flame polishing along the opposite end of the appliance. Intermittent cooling between flame polishing treatments will maintain the appliance at a temperature level to prevent distortion of the molded areas and maintain the integrity of the appliance.

As seen in FIG. 9, the blow pipe 19 is adjusted to have a shorter flame than as illustrated in FIG. 8 which also could be employed to effectively flame polish the appliance. Further, the appliance is shown with air holes to illustrate that flame polishing can be done without having an air hole insert in place.

The flame polishing treatment in this method is otherwise the same as that already described in connection with the method employed where the mold members are mounted in the appliance and which yields an optically clear appliance, as illustrated in FIG. 10 and designated as 21A.

While the heating step for causing the surface of the appliance to momentarily melt and become transparent is herein described as being accomplished by using a hot blue flame, it should be appreciated other heat sources capable of sufficiently raising the surface temperature of the appliance to cause glossing and effect transparentness could also be used. For example, superheated air or steam might be used.

It may be further appreciated that the elastomeric thermoplastic material used must be capable of being repeatedly heated to a level that will produce transparentness, such as being subjected to a flame impinging on its exterior surface which generates a localized heat.

From the foregoing, it will be appreciated that the method of the present invention is particularly useful for making a trimmed and buffed or trimmed custom appliance optically clear when molded from a resilient thermoplastic having the capability of having optically clear transparentness.

It will be understood that modifications and variations may be effected without departing from the scope of the novel concepts of the present invention, but it is understood that this application is to be limited only by the scope of the appended claims.

The invention is hereby claimed as follows:

1. A method of making a substantially optically clear custom tooth positioning and retaining appliance from a resilient thermoplastic material with the capability of having substantially optically clear transparentness, said appliance including air holes extending between the labial and lingual sides thereof and between the archways, wherein the appliance is molded of said material in a flask or mold having mounted therein upper and lower mold members for defining upper and lower archways in the appliance, trimmed on one or more grinding wheels, and optionally buff polished on a buffing wheel, after which the appliance has a semi-opaque or frosty appearance, said method comprising the steps of cooling the appliance to about room temperature or below, mounting an air hole insert in the air holes, and heat polishing the exterior surfaces of the appliance by applying localized heat to said surfaces at a level sufficient to cause momentary surface melting.

2. A method of making a substantially optically clear custom tooth positioning and retaining appliance from a resilient thermoplastic material with the capability of having substantially optically clear transparentness, wherein the appliance is molded of said material in a flask or mold having mounted therein upper and lower mold members for defining upper and lower archways in the appliance, trimmed on one or more grinding wheels, and optionally buff polished on a buffing wheel, after which the appliance has a semi-opaque or frosty appearance, said method comprising the steps of cooling the appliance to about room temperature or below, inserting the respective mold members or reproductions thereof into the respective molded archways of the appliance, and heat polishing the exterior surfaces of the appliance by applying localized heat to said surfaces at a level sufficient to cause momentary surface melting.

3. The method of claim 2, which further includes the steps of removing the mold members from the appliance, and flame polishing the archways.

4. The method of claim 2, which further includes the step of cooling the appliance with the mold members prior to the step of heat polishing.

5. The method of claim 4, wherein the step of cooling includes immersing the appliance with the mold members into cold water to wet and cool said mold members.

6. The method of claim 4, which further includes the step of blow drying the appliance and mold members prior to the step of heat polishing and subsequent to said step of cooling.

7. The method of claim 2, wherein said appliance further includes air holes extending between the labial and lingual sides of the appliance and between the archways, and said method further includes the step of mounting an air hole insert in the air holes prior to said heat polishing steps.

8. The method of claim 7, which further includes the step of cooling the appliance with the mold members prior to the step of heat polishing.

9. The method of claim 8, wherein the step of cooling includes immersing the appliance with the mold members into cold water to wet and cool said mold members.

10. The method of claim 9, which further includes the step of blow drying the appliance and mold members prior to the step of heat polishing and subsequent to said step of cooling.

11. A method of making a substantially optically clear custom tooth positioning and retaining appliance from a resilient thermoplastic material with the capability of having substantially optically clear transparentness, wherein the appliance is molded of said material in a flask or mold having mounted therein upper and lower mold members for defining upper and lower archways in the appliance, trimmed on one or more grinding wheels, and buff polished on a buffing wheel, after which the appliance has a semi-opaque or frosty appearance, said method comprising the steps of removing said mold members from the flask, inserting the respective mold members into the respective molded archways of the appliance, immersing the appliance with the mold members into cold water to wet and cool said mold members, blow drying the appliance and mold members, applying a concentrated hot flame across the exterior surfaces of the appliance until the surfaces take on a shiny appearance and during this application periodically cooling the appliance, and removing the mold members from the appliance.

12. The method of claim 11, which further includes the steps of applying concentrated hot flame across the surfaces of the archways until the surface shines and periodically cooling the appliance during said application.

13. The method of claim 12, wherein said material is a copolymer of ethylene and vinyl acetate.

* * * * *